US011571432B2

(12) United States Patent
Levin et al.

(10) Patent No.: US 11,571,432 B2
(45) Date of Patent: Feb. 7, 2023

(54) COMPOSITIONS THAT PREFERENTIALLY POTENTIATE SUBTYPES OF GABA$_A$ RECEPTORS AND METHODS OF USE THEREOF

(71) Applicant: Eliem Therapeutics, Inc., Boston, MA (US)

(72) Inventors: Andrew D. Levin, Newton, MA (US); Neil Buckley, Raleigh, NC (US)

(73) Assignee: Eliem Therapeutics (UK) Ltd, Altrincham (GB)

( * ) Notice: Subject to any disclaimer, the term of this patent is extended or adjusted under 35 U.S.C. 154(b) by 134 days.

(21) Appl. No.: 17/208,163

(22) Filed: Mar. 22, 2021

(65) Prior Publication Data
US 2021/0205332 A1 Jul. 8, 2021

Related U.S. Application Data

(63) Continuation of application No. 17/026,575, filed on Sep. 21, 2020, now Pat. No. 11,090,314, which is a continuation of application No. 16/587,157, filed on Sep. 30, 2019, now Pat. No. 10,857,163.

(51) Int. Cl.
*A61K 31/58* (2006.01)
*A61K 9/00* (2006.01)

(52) U.S. Cl.
CPC ............ *A61K 31/58* (2013.01); *A61K 9/0053* (2013.01)

(58) Field of Classification Search
CPC ...................................................... A61K 31/58
See application file for complete search history.

(56) References Cited

U.S. PATENT DOCUMENTS

| | | |
|---|---|---|
| 6,277,838 B1 | 8/2001 | Upasani et al. |
| 8,569,275 B2 | 10/2013 | Frincke |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,676,812 B2 | 6/2017 | Covey et al. |
| 9,725,481 B2 | 8/2017 | Martinez Botella et al. |
| 10,023,606 B2 | 7/2018 | Martinez Botella et al. |
| 10,172,871 B2 | 1/2019 | Martinez Botella et al. |
| 10,201,550 B2 | 2/2019 | Salituro et al. |
| 10,227,375 B2 | 3/2019 | Martinez Botella et al. |
| 10,246,482 B2 | 4/2019 | Harrison et al. |
| 10,259,840 B2 | 4/2019 | Harrison et al. |
| 10,322,139 B2 | 6/2019 | Reddy |
| 10,323,059 B2 | 6/2019 | Martinez Botella et al. |
| 10,329,320 B2 | 6/2019 | Robichaud et al. |
| 10,342,809 B2 | 7/2019 | Covey et al. |
| 10,342,810 B2 | 7/2019 | Martinez Botella et al. |
| 2003/0060425 A1 | 3/2003 | Ahlem et al. |
| 2005/0101581 A1 | 5/2005 | Reading et al. |
| 2006/0073099 A1 | 4/2006 | Frincke et al. |
| 2007/0053832 A1 | 3/2007 | Frincke et al. |
| 2007/0077201 A1 | 4/2007 | Reading et al. |
| 2007/0077203 A1 | 4/2007 | Garsd et al. |
| 2011/0212935 A1 | 9/2011 | Frincke |
| 2012/0178124 A1 | 7/2012 | Yamagishi et al. |
| 2014/0057885 A1 | 2/2014 | Reddy et al. |
| 2014/0235600 A1 | 8/2014 | Covey et al. |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0291654 A1 | 10/2015 | Upasani et al. |
| 2015/0315230 A1 | 11/2015 | Covey et al. |
| 2016/0022701 A1 | 1/2016 | Reddy et al. |
| 2016/0031930 A1 | 2/2016 | Martinez Botella et al. |
| 2016/0083417 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0152658 A1 | 6/2016 | Botella et al. |
| 2016/0229887 A1 | 8/2016 | Martinez Botella et al. |
| 2017/0152282 A9 | 6/2017 | Covey et al. |
| 2017/0190732 A1 | 7/2017 | Covey et al. |
| 2017/0232006 A1 | 8/2017 | Covey et al. |
| 2017/0233432 A1 | 8/2017 | Martinez Botella et al. |
| 2017/0233433 A1 | 8/2017 | Martinez Botella et al. |

(Continued)

FOREIGN PATENT DOCUMENTS

| | | |
|---|---|---|
| WO | 9521617 A1 | 8/1995 |
| WO | 9805337 A1 | 2/1998 |

(Continued)

OTHER PUBLICATIONS

Ghisdal, Determining the Relative Efficacy of Positive Allosteric Modulators of the GABAA Receptor: Design of a Screening Approach, Journal of Biomolecular Screening, 2014, vol. 19(3):462-467, Soc. Laboratory Automation and Screening.
International Search Report and Written Opinion issued in International Patent Application No. PCT/US2020/052167, dated Dec. 17, 2020, 6 pages.
Martinez Botella, Neuroactive Steroids. 2. 3a-Hydroxy-3b-methyl-21-(4-cyano-1H-pyrazol-1'-yl)-19-nor-5b-pregnan-20-one (SAGE-217): A Clinical Next Generation Neuroactive Steroid Positive Allosteric Modulator of the (g-Aminobutyric Acid)A Receptor, J. Med. Chem. 2017, 60, 781077819, American Chemical Society, USA.
Sigel, Structure, Function, and Modulation of GABAA Receptors, J. Biol. Chem. 2012, 287(48): 40224-40231, Am Soc. Biochem. Mol. Biol. USA.
Tian, A Clinically Applicable Positive Allosteric Modulator of GABA Receptors Promotes Human β-Cell Replication and Survival as well as GABA's Ability to Inhibit Inflammatory T Cells, J. Diabetes Res. 2019, Article ID 5783545 (7 pages).
Tian, Clinically applicable GABA receptor positive allosteric modulators promote b-cell replication, Scientific Reports, Mar. 23, 2017;7(1):374 (7 pages).

*Primary Examiner* — San Ming R Hui
(74) *Attorney, Agent, or Firm* — Brown Rudnick LLP; Adam M. Schoen

(57) ABSTRACT

The invention provides compositions containing isomerically pure forms of neurosteroids that permit preferential modulation of different subtypes of GABA$_A$ receptors, such as preferential modulation of α4β3δ GABA$_A$ receptors over α1β2γ2 GABA$_A$ receptors. The invention also provides methods of treating GABA$_A$ disorders using such compositions.

10 Claims, No Drawings

(56) References Cited

U.S. PATENT DOCUMENTS

| | | |
|---|---|---|
| 2017/0240589 A1 | 8/2017 | Martinez Botella et al. |
| 2017/0246191 A1 | 8/2017 | Martinez Botella et al. |
| 2017/0247405 A1 | 8/2017 | Harrison et al. |
| 2017/0247406 A1 | 8/2017 | Harrison et al. |
| 2017/0304321 A1 | 10/2017 | Quirk et al. |
| 2017/0305960 A1 | 10/2017 | Martinez Botella et al. |
| 2017/0319695 A1 | 11/2017 | Robichaud et al. |
| 2017/0342102 A1 | 11/2017 | Martinez Botella et al. |
| 2017/0342103 A1 | 11/2017 | Upasani et al. |
| 2017/0348326 A1 | 12/2017 | Reddy |
| 2017/0348327 A1 | 12/2017 | Kanes et al. |
| 2018/0037602 A1 | 2/2018 | Robichaud et al. |
| 2018/0051052 A1 | 2/2018 | Martinez Botella et al. |
| 2018/0141971 A1 | 5/2018 | Martinez Botella et al. |
| 2018/0179247 A1 | 6/2018 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0215779 A1 | 8/2018 | Martinez Botella et al. |
| 2018/0237470 A1 | 8/2018 | Martinez Botella et al. |
| 2018/0296487 A1 | 10/2018 | Saporito et al. |
| 2018/0311258 A1 | 11/2018 | Robichaud et al. |
| 2018/0311262 A1 | 11/2018 | Martinez Botella et al. |
| 2018/0362573 A1 | 12/2018 | Upasani et al. |
| 2019/0008873 A1 | 1/2019 | Salituro et al. |
| 2019/0038639 A1 | 2/2019 | Reddy et al. |
| 2019/0112331 A1 | 4/2019 | Botella et al. |
| 2019/0125764 A1 | 5/2019 | Salituro et al. |
| 2019/0127414 A1 | 5/2019 | Martinez Botella et al. |
| 2019/0135854 A1 | 5/2019 | Harrison et al. |
| 2019/0169226 A1 | 6/2019 | Harrison et al. |
| 2019/0177358 A1 | 6/2019 | Martinez Botella et al. |
| 2019/0177359 A1 | 6/2019 | Watson et al. |

FOREIGN PATENT DOCUMENTS

| | | |
|---|---|---|
| WO | 2001/030802 A2 | 5/2001 |
| WO | 2002/069977 A1 | 9/2002 |
| WO | 2004/019953 A1 | 3/2004 |
| WO | 2006/037016 A2 | 4/2006 |
| WO | 2006/110172 A2 | 10/2006 |
| WO | 2013/036835 A1 | 3/2013 |
| WO | 2013/056181 A1 | 4/2013 |
| WO | 2013/112605 A2 | 8/2013 |
| WO | 2013/188792 A2 | 12/2013 |
| WO | 2014/018375 A1 | 1/2014 |
| WO | 2014/031792 A2 | 2/2014 |
| WO | 2014/100228 A1 | 6/2014 |
| WO | 2014/160441 A1 | 10/2014 |
| WO | 2014/160480 A1 | 10/2014 |
| WO | 2014/169831 A1 | 10/2014 |
| WO | 2014/169832 A1 | 10/2014 |
| WO | 2014/169833 A1 | 10/2014 |
| WO | 2014/169836 A1 | 10/2014 |
| WO | 2015/010054 A2 | 1/2015 |
| WO | 2015/027227 A1 | 2/2015 |
| WO | 2015/180679 A1 | 12/2015 |
| WO | 2015/195962 A1 | 12/2015 |
| WO | 2015/195967 A1 | 12/2015 |
| WO | 2016/040322 A1 | 3/2016 |
| WO | 2016/057713 A1 | 4/2016 |
| WO | 2016/061527 A1 | 4/2016 |
| WO | 2016/061537 A1 | 4/2016 |
| WO | 2016/082789 A1 | 6/2016 |
| WO | 2016/123056 A1 | 8/2016 |
| WO | 2016/134301 A2 | 8/2016 |
| WO | 2016/164763 A1 | 10/2016 |
| WO | 2016/205721 A1 | 12/2016 |
| WO | 2017/007832 A1 | 1/2017 |
| WO | 2017/007836 A1 | 1/2017 |
| WO | 2017/007840 A1 | 1/2017 |
| WO | 2017/066626 A1 | 4/2017 |
| WO | 2017/087864 A1 | 5/2017 |
| WO | 2017/156103 A1 | 9/2017 |
| WO | 2017/173358 A1 | 10/2017 |
| WO | 2017/187343 A2 | 11/2017 |
| WO | 2017/193046 A1 | 11/2017 |
| WO | 2018/009867 A1 | 1/2018 |
| WO | 2018/013613 A1 | 1/2018 |
| WO | 2018/013615 A1 | 1/2018 |
| WO | 2018/039378 A1 | 3/2018 |
| WO | 2018/064649 A1 | 4/2018 |
| WO | 2018/071803 A1 | 4/2018 |
| WO | 2018/075698 A1 | 4/2018 |
| WO | 2018/075699 A1 | 4/2018 |
| WO | 2018/195186 A1 | 10/2018 |
| WO | 2018/227129 A1 | 12/2018 |
| WO | 2019/018119 A1 | 1/2019 |
| WO | 2019/051264 A1 | 3/2019 |
| WO | 2019/051477 A1 | 3/2019 |
| WO | 2019/055764 A1 | 3/2019 |
| WO | 2019/075361 A1 | 4/2019 |
| WO | 2019/075362 A1 | 4/2019 |
| WO | 2019/113494 A1 | 6/2019 |
| WO | 2019/126741 A1 | 6/2019 |
| WO | 2019/126761 A1 | 6/2019 |
| WO | 2019/140272 A1 | 7/2019 |
| WO | 2020/210116 A1 | 10/2020 |

COMPOSITIONS THAT PREFERENTIALLY POTENTIATE SUBTYPES OF GABA$_A$ RECEPTORS AND METHODS OF USE THEREOF

This application is a continuation of U.S. Non-provisional application Ser. No. 17/026,575, filed Sep. 21, 2020, which claims the benefit of, and priority to, U.S. Non-provisional application Ser. No. 16/587,157, filed Sep. 30, 2019, the contents of each of which are incorporated by reference.

FIELD OF THE INVENTION

The invention relates generally to compositions containing neurosteroids and methods of using the same to treat GABA$_A$ disorders in a subject.

BACKGROUND

According the World Health Organization (WHO), neurological disorders affect up to one billion people worldwide. Neurological disorders include a wide range of conditions, such as Alzheimer's disease, brain injuries, epilepsy, headache, infections, multiple sclerosis, and Parkinson's disease, and stroke. Many neurological disorders stem from altered signaling by receptors for the neurotransmitter γ-aminobutyric acid (GABA). GABA$_A$ receptors are pentameric transmembrane receptors that include various combinations of 19 different subunit polypeptides. At least 15 GABA$_A$ receptor subtypes are known, and particular subtypes are associated with different conditions. For example, altered activity of receptor subtypes that include $\alpha_2$ or $\alpha_3$ subunits is associated with anxiety disorders, whereas $\alpha_5$-containing subtypes appear to play a role in memory and cognition.

Neuroactive steroids that alter the activity of GABA$_A$ receptors have been investigated as drug candidates for a variety of neurological disorders. However, the therapeutic potential of such molecules remains largely untapped. One reason for the shortfall is that the large number of chemical variants that can be made from the steroid structural core makes it difficult to know whether compounds currently being investigated have superior pharmacological properties to other molecules that have not yet been made or analyzed. Another issue is that the structural similarity of different GABA$_A$ receptor subtypes makes it challenging to identify molecules with a desired subtype specificity. Consequently, millions of people continue to suffer from neurological conditions due to the limited arsenal of neuroactive steroids currently at our disposal.

SUMMARY

The invention provides compositions that contain isomerically pure forms of selected neurosteroids. The invention recognizes that interactions between neurosteroids and GABA$_A$ receptors are highly sensitive to the stereochemical structure of the neurosteroids and that certain neurosteroids display strong GABA$_A$ receptor subtype specificity when provided in compositions that are substantially free of isomeric contaminants. Because the compositions of the invention selectively target particular GABA$_A$ receptor subtypes, they have greatly improved pharmacological efficacy over prior compositions, including those that contain biologically active compounds contaminated with isomers that are less active.

In a particular embodiment, the invention provides compositions that contain an isomerically pure form of a compound of Formula (I):

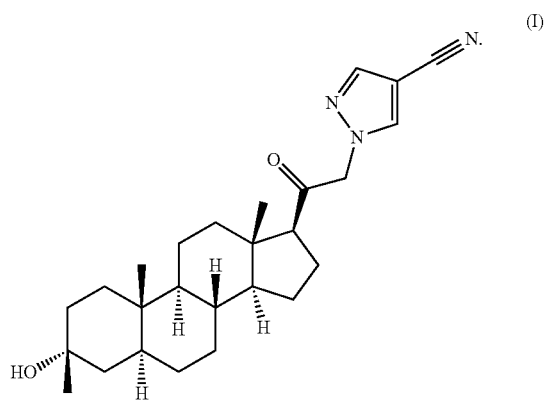

The present invention includes the finding that isomerically pure compositions of Formula (I) are considerably more active on α4β3δ GABA$_A$ receptors than on α1β2γ2 GABA$_A$ receptors. As described herein, such compositions modulate the activity of α4β3δ receptors with an EC$_{50}$ at least 5-fold lower than for α1β2γ2 receptors. Without wishing to be bound by a particular theory, it is believed that the stereochemical configurations at all of the chiral centers of the molecule and the atomic bonding patterns within the molecule are important in conferring GABA$_A$ receptor subtype selectivity. Thus, mixtures that contain the compound of Formula (I) together with isomers thereof, such as regioisomers of Formula (I) or stereoisomers that differ structurally from Formula (I) at only a single chiral center, lack such selectivity. Because compositions that contain an isomerically pure form of the compound of Formula (I) preferentially target α4β3δ GABA$_A$ receptors, they are useful for therapeutic applications in which altering the activity of this receptor is beneficial.

In an aspect, the invention provides pharmaceutical compositions containing an isomerically pure form of a compound of Formula (I):

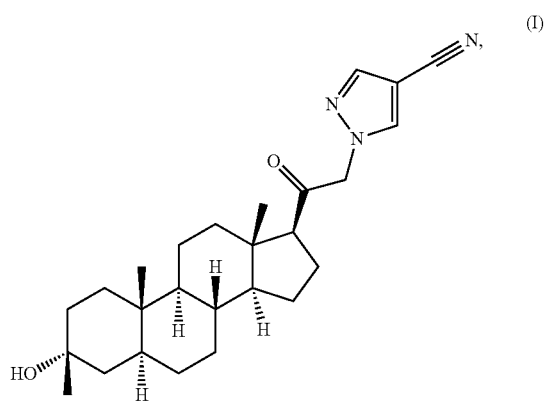

wherein the compound of Formula (I) is present in a therapeutically effective amount to preferentially potentiate an α4β3δ GABA$_A$ receptor as compared to an α1β2γ2 GABA$_A$ receptor.

In another aspect, the invention provides methods for treating a GABA$_A$ disorder by providing to a subject a pharmaceutical composition comprising an isomerically pure form of a compound of Formula (I):

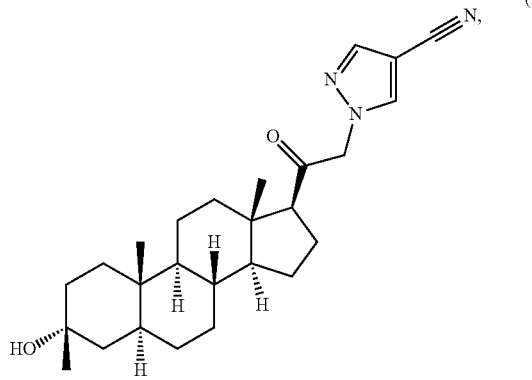

(I)

wherein the compound of Formula (I) is present in a therapeutically effective amount to preferentially potentiate an α4β3δ GABA$_A$ receptor as compared to an α1β2γ2 GABA$_A$ receptor.

The composition may be chemically pure, i.e., free from other molecules or chemical species. For example, the other molecule or chemical species may have a distinct chemical formula, structural formula, empirical formula, molecular formula, or condensed formula. The composition may have a defined level of chemical purity. For example, the compound of Formula (I) may be present at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the total amount of a mixture that includes the compound of Formula (I) and one or more distinct molecules or chemical species.

The composition may be isomerically pure with respect to all isomers. The composition may be isomerically pure with respect to one or more particular types of isomers. The composition may be substantially free of structural isomers or a particular type of structural isomers, such as a regioisomers. The composition may be substantially free of stereoisomers or a particular type of stereoisomers, such as enantiomers or diastereomers.

The composition may contain the compound of Formula (I) at any level of isomeric purity to achieve preferential modulation of an α4β3δ GABA$_A$ receptor as compared to an α1β2γ2 GABA$_A$ receptor. For example, the compound of Formula (I) may be present at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the total amount of isomeric molecules that include the compound of Formula (I) and an isomer thereof.

The composition may contain the compound of Formula (I) and be substantially free of stereoisomers. The stereoisomer may differ from Formula (I) at one, two, three, four, five, six, seven, or eight chiral centers. The stereoisomer may be a diastereomer or an enantiomer. For example, the stereoisomer may be a compound of Formulas (II) or (III):

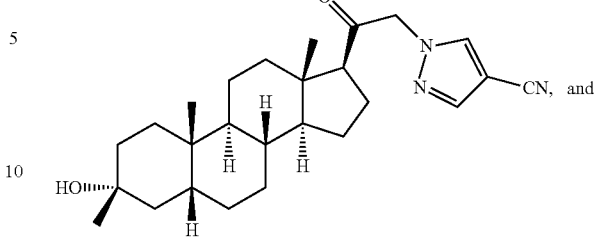

(II)

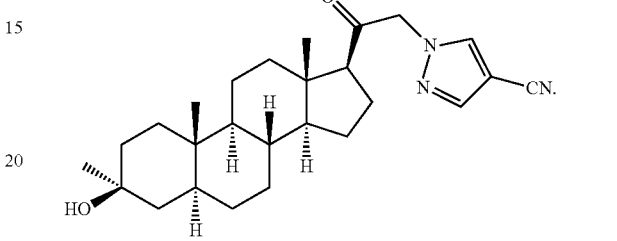

(III)

The composition may contain one or more stereoisomers of the compound of Formula (I), such as a compound of Formula (II) or (III), at less than 5%, less than 4%, less than 3%, less than 2%, less than 1%, less than 0.5%, or less than 0.1% of the total of the compound of Formula (I) and the one or more stereoisomers thereof. The composition may contain the compound of Formula (I) and one or more stereoisomer thereof at a ratio of at least 19:1, 20:1, 25:1, 30:1, 40:1, 50:1, 100:1, 200:1, 500:1, or 1000:1.

The compound may potentiate a GABA$_A$ receptor, a GABA$_A$ receptor subtypes, or a subset of GABA$_A$ receptor subtypes by any mechanism. The compound may potentiate a GABA$_A$ receptor, subtype, or subset by allosteric modulation, activation, or inhibition. The allosteric modulation may be positive or negative.

The composition may preferentially potentiate an α4β3δ GABA$_A$ receptor as compared to an α1β2γ2 GABA$_A$ receptor to any degree. The composition may preferentially potentiate an α4β3δ GABA$_A$ receptor as compared to an α1β2γ2 GABA$_A$ receptor by any measure or parameter. The composition may have an EC$_{50}$ for α4β3δ GABA$_A$ receptors that is lower than the EC$_{50}$ for α1β2γ2 GABA$_A$ receptors. The EC$_{50}$ for α4β3δ GABA$_A$ receptors may be lower than the EC$_{50}$ for α1β2γ2 GABA$_A$ receptors by about 2-fold, about 3-fold, about 4-fold, about 5-fold, about 6-fold, about 7-fold, about 8-fold, about 10-fold, about 20-fold, about 50-fold, about 100-fold, about 200-fold, about 500-fold, or about 1000-fold. The EC$_{50}$ for α4β3δ GABA$_A$ receptors may be less than about 50%, less than about 40%, less than about 30%, less than about 25%, less than about 20%, less than about 15%, less than about 10%, less than about 5%, less than about 4%, less than about 3%, less than about 2%, less than about 1%, less than about 0.5%, less than about 0.2%, or less than about 0.1% of the EC$_{50}$ for α1β2γ2 GABA$_A$ receptors.

The composition may have a binding affinity (which may be expressed, e.g., as a dissociation constant K$_D$) for α4β3δ GABA$_A$ receptors that is lower than the binding affinity for α1β2γ2 GABA$_A$ receptors. The binding affinity for α4β3δ GABA$_A$ receptors may be lower than the binding affinity for α1β2γ2 GABA$_A$ receptors by about 2-fold, about 3-fold, about 4-fold, about 5-fold, about 6-fold, about 7-fold, about 8-fold, about 10-fold, about 20-fold, about 50-fold, about 100-fold, about 200-fold, about 500-fold, or about 1000-fold. The binding affinity for α4β3δ GABA$_A$ receptors may be less than about 50%, less than about 40%, less than about 30%, less than about 25%, less than about 20%, less than about 15%, less than about 10%, less than about 5%, less than about 4%, less than about 3%, less than about 2%, less than about 1%, less than about 0.5%, less than about 0.2%, or less than about 0.1% of the binding affinity for α1β2γ2 GABA$_A$ receptors.

The composition may have an EC$_{50}$ for α4β3δ GABA$_A$ receptors that is below a defined value. The composition may have an EC$_{50}$ for α4β3δ GABA$_A$ receptors that is less than about 1 less than about 500 nM, less than about 400 nM, less than about 300 nM, less than about 200 nM, less than about 100 nM, less than about 50 nM, less than about 25 nM, less than about 10 nM, less than about 5 nM, less than about 2.5 nM, less than about 1 nM, less than about 0.5 nM, less than about 0.25 nM, or less than about 0.1 nM.

The composition may have a binding affinity for α4β3δ GABA$_A$ receptors that is below a defined value. The composition may have an binding affinity for α4β3δ GABA$_A$ receptors that is less than about 1 less than about 500 nM, less than about 400 nM, less than about 300 nM, less than about 200 nM, less than about 100 nM, less than about 50 nM, less than about 25 nM, less than about 10 nM, less than about 5 nM, less than about 2.5 nM, less than about 1 nM, less than about 0.5 nM, less than about 0.25 nM, or less than about 0.1 nM.

The composition may be effective for treatment of a GABA$_A$ disorder. The GABA$_A$ disorder may be any disease, disorder, or condition associated with altered GABA$_A$ receptor function or any disorder may be disease, disorder, or condition that can be ameliorated by altered GABA$_A$ receptor function. The GABA$_A$ disorder may be acute pain, an addictive disorder, Alzheimer's disease, Angelman's syndrome, anti-social personality disorder, an anxiety disorder, attention deficit hyperactivity disorder (ADHD), an attention disorder, an auditory disorder, autism, an autism spectrum disorder, bipolar disorder, chronic pain, a cognitive disorder, a compulsive disorder, a convulsive disorder, dementia, depression, dysthymia, an epileptic disorder, essential tremor, epileptogenesis, fragile X syndrome, generalized anxiety disorder (GAD), Huntington's disease, injury related pain syndrome, insomnia, ischemia, Lewis body type dementia, a memory disorder, migraines, a mood disorder, movement disorder, a neurodegenerative disease, neuropathic pain, an obsessive compulsive disorder, pain, a panic disorder, Parkinson's disease, a personality disorder, post-traumatic stress disorder (PTSD), psychosis, Rett syndrome, a schizoaffective disorder, schizophrenia, a schizophrenia spectrum disorder, a seizure disorder, a sleep disorder, social anxiety disorder, status epilepticus, stress, stroke, tinnitus, traumatic brain injury (TBI), vascular disease, vascular malformation, vascular type dementia movement disorder, Wilson's disease, or withdrawal syndrome.

The composition may be formulated for administration by a particular mechanism. The composition may be formulated for oral, intravenous, enteral, parenteral, dermal, buccal, topical nasal, or pulmonary administration. The composition may be formulated for administration by injection or on an implantable medical device (e.g., stent or drug-eluting stent or balloon equivalents).

The composition may be formulated a single daily dosage. The composition may be formulated for multiple daily dosages, e.g., two, three, four, five, six or more daily dosages.

The composition may be provided to the subject according to any dosing schedule. The composition may be provided once per day. The composition may be provided multiple times per day. The composition may be provided two time, three times, four times, five times, six times, or more per day.

DETAILED DESCRIPTION

The invention provides compositions that contain isomerically pure forms of neurosteroids and methods of using such compositions to treat neurological and other disorders. The invention is based on the recognition that isomerically pure neurosteroids allow modulation of specific subtypes of γ-aminobutyric acid (GABA) receptors. Because the compositions permit selective modulation of subtypes of GABA receptors, they are useful for treating conditions in which alteration of those receptor subtypes provides therapeutic benefit.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

As used herein, a "pure isomeric" compound or "isomerically pure" compound is substantially free of other isomers of the compound. The term "pure isomeric" compound or "isomerically pure" denotes that the compound comprises at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the compound with the specified structure. In certain embodiments, the weights are based upon total weight of all isomers of the compound.

As used herein, a "pure stereoisomeric" compound or "stereoisomerically pure" compound is substantially free of other stereoisomers of the compound. Thus, the composition is substantially free of isomers that differ at any chiral center. If the compound has multiple chiral centers, a substantial majority of the composition contains compounds having identical stereochemistry at all of the chiral centers. The term "pure stereoisomeric" compound or "stereoisomerically pure" denotes that the compound comprises at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the compound with the specified stereochemistry. In certain embodiments, the weights are based upon total weight of all stereoisomers of the compound.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the enantiomer. In certain embodiments, the weights are based upon total weight of all enantiomers or stereoisomers of the compound.

Compounds described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; N may be any isotopic form, including $^{14}N$ and $^{15}N$; O may be in any isotopic form, including $^{16}O$ and $^{18}O$; and the like.

The articles "a" and "an" may be used herein to refer to one or to more than one (i.e. at least one) of the grammatical objects of the article. By way of example "an analogue" means one analogue or more than one analogue.

As used herein, the terms "modulation" and "potentiation" refer to the inhibition or stimulation of GABA receptor function. A "modulator" or "potentiator" may be, for example, an agonist, partial agonist, antagonist, or partial antagonist of the GABA receptor. The "modulator" or "potentiator" may act at the active site or at an allosteric site on a GABA receptor. It may promote or inhibit ligand binding. It may facilitate or attenuate ligand-mediated, e.g., GABA-mediated, signaling.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, el al., J. Pharm. Sci. (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$, and $^{13}N$, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers", and those that are non-superimposable mirror images of each other are termed "enantiomers." When a compound has an asymmetric center, for example, and an atom, such as a carbon atom, is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of n electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, a human (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Compositions

Compounds

The invention provides compositions with isomerically pure forms of neuro steroids.

In certain embodiments, the invention provides pharmaceutical compositions containing an isomerically pure form of a compound of Formula (I):

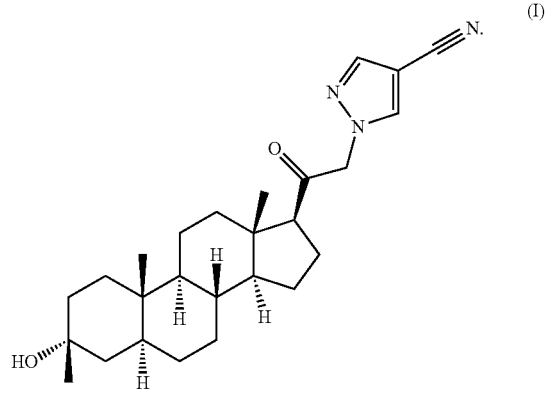

The composition may be chemically pure, i.e., free from other molecules or chemical species. For example, the other molecule or chemical species may have a distinct chemical formula, structural formula, empirical formula, molecular formula, or condensed formula. The composition may have a defined level of chemical purity. For example, the compound of Formula (I) may be present at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the total amount of a mixture that includes the compound of Formula (I) and one or more distinct molecules or chemical species.

The composition may contain the compound of Formula (I) at any level of isomeric purity, i.e., the composition may contain the compound of Formula (I) at a level in relation to an isomeric form of the compound. For example, the compound of Formula (I) may be present at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the total amount of isomeric molecules that include the compound of Formula (I) and an isomer thereof.

The composition may be isomerically pure with respect to all isomers. The composition may be isomerically pure with respect to one or more particular types of isomers. The composition may be substantially free of structural isomers or a particular type of structural isomers, such as a regioisomers. The composition may be substantially free of stereoisomers or a particular type of stereoisomers, such as enantiomers or diastereomers.

The composition may contain the compound of Formula (I) at any level of isomeric purity to achieve preferential modulation of an α4β3δ $GABA_A$ receptor as compared to an α1β2γ2 GABA$_A$ receptor. For example, the compound of Formula (I) may be present at at least 95% by weight, at least 96% by weight, at least 97% by weight, at least 98% by weight, at least 99% by weight, at least 99.5% by weight, at least 99.6% by weight, at least 99.7% by weight, at least 99.8% by weight, or at least 99.9% by weight of the total amount of isomeric molecules that include the compound of Formula (I) and an isomer thereof.

The composition may contain the compound of Formula (I) and be substantially free of stereoisomers. The stereoisomer may differ from Formula (I) at one, two, three, four, five, six, seven, or eight chiral centers. The stereoisomer may be a diastereomer or an enantiomer. For example, the stereoisomer may be a compound of Formulas (II) or (III):

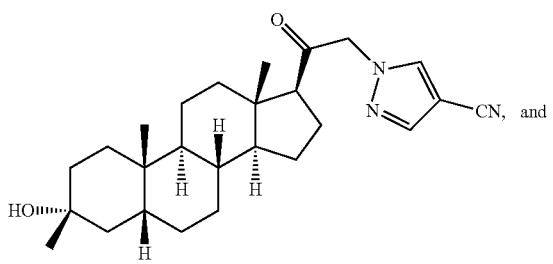

(II)

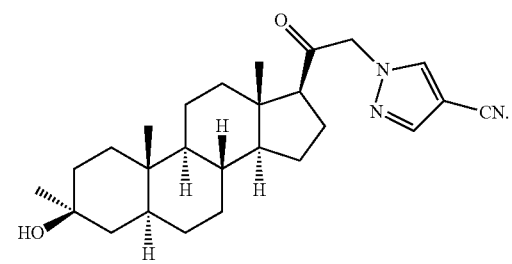

(III)

The composition may contain one or more stereoisomers of the compound of Formula (I), such as a compound of Formula (II) or (III), at less than 5%, less than 4%, less than 3%, less than 2%, less than 1%, less than 0.5%, or less than 0.1% of the total of the compound of Formula (I) and the one or more stereoisomers thereof. The composition may contain the compound of Formula (I) and one or more stereoisomer thereof at a ratio of at least 19:1, 20:1, 25:1, 30:1, 40:1, 50:1, 100:1, 200:1, 500:1, or 1000:1.

Formulations

The invention provides pharmaceutical compositions containing one or more of the compounds described above. A pharmaceutical composition containing the compounds may be in a form suitable for oral use, for example, as tablets, troches, lozenges, fast-melts, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and 4,265,874, the contents of which are incorporated herein by reference, to form osmotic therapeutic tablets for control release. Preparation and administration of compounds is discussed in U.S. Pat. No. 6,214,841 and U.S. Pub. No. 2003/0232877, the contents of which are incorporated herein by reference.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

In certain embodiments, the formulation is not a sustained release formulation. In certain embodiments, the formulation is not injectable. In certain embodiments, the formulation does not contain particles having a D50 (volume weighted median diameter) of less than 10 microns. In certain embodiments, the formulation does not contain a polymer surface stabilizer. In certain embodiments, the formulation is not an aqueous suspension.

The composition may be formulated for administration by a particular mechanism. The composition may be formulated for oral, intravenous, enteral, parenteral, dermal, buccal, topical nasal, or pulmonary administration. The composition may be formulated for administration by injection or on an implantable medical device (e.g., stent or drug-eluting stent or balloon equivalents).

The composition may be formulated a single daily dosage. The composition may be formulated for multiple daily dosages, e.g., two, three, four, five, six or more daily dosages.

The composition may be provided to the subject according to any dosing schedule. The composition may be provide once per day. The composition may be provided multiple times per day. The composition may be provided two time, three times, four times, five times, six times, or more per day.

Treatment of $GABA_A$ Receptor Disorders

The compositions of the invention are useful for treating disorders that are associated with, or can be ameliorated by, alteration of activity of a $GABA_A$ receptor. $GABA_A$ receptors are ligand-gated ion channels that selectively allow Cl⁻ ions to pass through the plasma membrane upon binding of GABA. $GABA_A$ receptors are expressed in neurons throughout the central nervous system (CNS) and mediate most of the physiological activities of GABA in the CNS. Within neurons, the type and density of $GABA_A$ receptors can vary between cell bodies and dendrites. $GABA_A$ receptors are also expressed in other tissues, including Leydig cells, placenta, immune cells, liver, bone growth plates, and other endocrine tissues. Outside the CNS, $GABA_A$ receptors can regulate cell proliferation and immune responses.

Structurally, $GABA_A$ receptors are pentamers that include five polypeptide subunits. The polypeptide subunits are encoded by 19 genes that are grouped as follows based on sequence similarity: $\alpha(1-6)$, $\beta(1-3)$, $\gamma(1-3)$, $\delta$, $\varepsilon$, $\theta$, $\pi$, and $\rho(1-3)$. Most subtypes are heteropentamers that include two copies of one type of $\alpha$ subunit, two copies of one type of $\beta$ subunit, and one copy of one type of $\gamma$, $\delta$, $\varepsilon$, $\theta$, or $\pi$ subunit; other subtypes are homopentamers or heteropentamers of $\rho$ subunits. Known subtypes of $GABA_A$ receptors include $\alpha1\beta1\gamma2$, $\alpha1\beta2\gamma2$, $\alpha1\beta3\gamma2$, $\alpha2\beta1\gamma2$, $\alpha2\beta2\gamma2$, $\alpha2\beta3\gamma2$, $\alpha3\beta1\gamma2$, $\alpha3\beta2\gamma2$, $\alpha3\beta3\gamma2$, $\alpha4\beta1\gamma2$, $\alpha4\beta3\delta$, $\alpha4\beta3\gamma2$, $\alpha5\beta1\gamma2$, $\alpha5\beta2\gamma2$, $\alpha5\beta3\gamma2$, $\alpha6\beta1\gamma2$, $\alpha6\beta2\gamma2$, and $\alpha6\beta3\gamma2$. $GABA_A$ receptor subtypes vary among tissue types and anatomical regions of the CNS, and subtypes may be associated with specific functions. In addition, $GABA_A$ receptor subtypes may vary between normal and malignant cells of the same tissue type.

The active site of a $GABA_A$ receptor is the binding site for GABA and for drugs such as muscimol, gaboxadol, and bicuculline. $GABA_A$ receptors also have several allosteric binding sites that are the targets of other drugs, including benzodiazepines, nonbenzodiazepines, neuroactive steroids, barbiturates, ethanol, inhaled anaesthetics, and picrotoxin. Thus, the activity of $GABA_A$ receptors is controlled by binding of molecules to both the active and allosteric binding sites. The structure, function, and regulation of $GABA_A$ receptors are known in the art and described in, for example, Sigel E., and Steinmann, M. E., Structure, Function, and Modulation of $GABA_A$ Receptors, J. Biol. Chem. 287:48 pp. 40224-402311 (2012), doi: 10.1074/jbc.R112.386664, the contents of which are incorporated herein by reference.

The isomerically pure compositions of the invention preferentially potentiate the activity selected $GABA_A$ receptor subtypes. The compositions of the invention may preferentially potentiate the activity of one or more $GABA_A$ receptor subtypes, such as those described above, relative to one or more $GABA_A$ receptor subtypes. In certain embodiments, the compositions preferentially potentiate the activity of $\alpha4\beta3\delta$ receptors compared to $\alpha1\beta2\gamma2$ receptors.

The compositions of the invention may potentiate one or more $GABA_A$ receptors by any mechanism. For example, and without limitation, the isomerically pure form a compound may potentiate a $GABA_A$ receptor by allosteric modulation, activation, or inhibition. The allosteric modulation may be positive or negative.

The preferential activity of a composition on one or more $GABA_A$ receptor as compared to one or more other $GABA_A$ receptor may be measured by any suitable means. Activity may be measure using in vitro assays or in vivo assays. For example and without limitation, methods of measuring the effect of modulators on $GABA_A$ receptor activity include anticonvulsant assays, binding assays, fluorescence membrane potential assays, immune response assays, intracranial self-stimulation assays patch clamps assays, proliferation assays receptor occupancy assays seizure induction assays, e.g., using pentylenetetrazol (PTZ) or maximal electroshock (MES), and survival assays. Such assays are known in the art and described in, for example, International Publication No. WO 2016/061527; Ghisdal P., et al., Determining the relative efficacy of positive allosteric modulators of the $GABA_A$ receptor: design of a screening approach, J Biomol Screen. 2014 March; 19(3):462-7. doi: 10.1177/1087057113501555, Epub 2013 Aug. 29; Tian J., et al., Clinically applicable GABA receptor positive allosteric modulators promote β-cell replication, Sci Rep. 2017 Mar. 23; 7(1):374. doi: 10.1038/s41598-017-00515-y; and Tian J., et al., A Clinically Applicable Positive Allosteric Modulator of GABA Receptors Promotes Human β-Cell Replication and Survival as well as GABA's Ability to Inhibit Inflammatory T Cells, J Diabetes Res. 2019 Feb. 26; 2019:5783545, doi: 10.1155/2019/5783545, the contents of each of which are incorporated herein by reference.

The preferential activity of a composition on one or more $GABA_A$ receptors as compared to one or more other $GABA_A$ receptors may be expressed by any suitable means. For example and without limitation, the preferential activity may be indicated by a comparison of $EC_{50}$ values or binding affinity values.

In certain embodiments, compositions of the invention have an $EC_{50}$ for α4β3δ $GABA_A$ receptors that is lower than the $EC_{50}$ for α1β2γ2 $GABA_A$ receptors. The $EC_{50}$ for α4β3δ $GABA_A$ receptors may be lower than the $EC_{50}$ for α1β2γ2 $GABA_A$ receptors by about 2-fold, about 3-fold, about 4-fold, about 5-fold, about 6-fold, about 7-fold, about 8-fold, about 10-fold, about 20-fold, about 50-fold, about 100-fold, about 200-fold, about 500-fold, or about 1000-fold.

In certain embodiments, compositions of the invention have an $EC_{50}$ for α4β3δ $GABA_A$ receptors that is less than about 50%, less than about 40%, less than about 30%, less than about 25%, less than about 20%, less than about 15%, less than about 10%, less than about 5%, less than about 4%, less than about 3%, less than about 2%, less than about 1%, less than about 0.5%, less than about 0.2%, or less than about 0.1% of the $EC_{50}$ for α1β2γ2 $GABA_A$ receptors.

In certain embodiments, compositions of the invention have an binding affinity (which may be expressed, e.g., as a dissociation constant $K_D$) for α4β3δ $GABA_A$ receptors that is lower than the binding affinity for α1β2γ2 $GABA_A$ receptors. The binding affinity for α4β3δ $GABA_A$ receptors may be lower than the binding affinity for α1β2γ2 $GABA_A$ receptors by about 2-fold, about 3-fold, about 4-fold, about 5-fold, about 6-fold, about 7-fold, about 8-fold, about 10-fold, about 20-fold, about 50-fold, about 100-fold, about 200-fold, about 500-fold, or about 1000-fold.

In certain embodiments, compositions of the invention have an binding affinity for α4β3δ $GABA_A$ receptors that is less than about 50%, less than about 40%, less than about 30%, less than about 25%, less than about 20%, less than about 15%, less than about 10%, less than about 5%, less than about 4%, less than about 3%, less than about 2%, less than about 1%, less than about 0.5%, less than about 0.2%, or less than about 0.1% of the binding affinity for α1β2γ2 $GABA_A$ receptors.

In certain embodiments, compositions of the invention have an $EC_{50}$ for α4β3δ $GABA_A$ receptors that is below a defined value. For example and without limitation, the composition may have an $EC_{50}$ for α4β3δ $GABA_A$ receptors that is less than about 1 less than about 500 nM, less than about 400 nM, less than about 300 nM, less than about 200 nM, less than about 100 nM, less than about 50 nM, less than about 25 nM, less than about 10 nM, less than about 5 nM, less than about 2.5 nM, less than about 1 nM, less than about 0.5 nM, less than about 0.25 nM, or less than about 0.1 nM.

In certain embodiments, compositions of the invention have an binding affinity for α4β3δ $GABA_A$ receptors below a defined value. For example and without limitation, the composition may have an binding affinity for α4β3δ $GABA_A$ receptors that is less than about 1 less than about 500 nM, less than about 400 nM, less than about 300 nM, less than about 200 nM, less than about 100 nM, less than about 50 nM, less than about 25 nM, less than about 10 nM, less than about 5 nM, less than about 2.5 nM, less than about 1 nM, less than about 0.5 nM, less than about 0.25 nM, or less than about 0.1 nM.

The compositions and methods of the invention may be effective for treatment of a $GABA_A$ disorder. The $GABA_A$ disorder may be any disease, disorder, or condition associated with altered $GABA_A$ receptor function or any disorder may be disease, disorder, or condition that can be ameliorated by altered $GABA_A$ receptor function. The $GABA_A$ disorder may be acute pain, an addictive disorder, Alzheimer's disease, Angelman's syndrome, anti-social personality disorder, an anxiety disorder, attention deficit hyperactivity disorder (ADHD), an attention disorder, an auditory disorder, autism, an autism spectrum disorder, bipolar disorder, chronic pain, a cognitive disorder, a compulsive disorder, a convulsive disorder, dementia, depression, dysthymia, an epileptic disorder, essential tremor, epileptogenesis, fragile X syndrome, generalized anxiety disorder (GAD), Huntington's disease, injury related pain syndrome, insomnia, ischemia, Lewis body type dementia, a memory disorder, migraines, a mood disorder, movement disorder, a neurodegenerative disease, neuropathic pain, an obsessive compulsive disorder, pain, a panic disorder, Parkinson's disease, a personality disorder, posttraumatic stress disorder (PTSD), psychosis, Rett syndrome, a schizoaffective disorder, schizophrenia, a schizophrenia spectrum disorder, a seizure disorder, a sleep disorder, social anxiety disorder, status epilepticus, stress, stroke, tinnitus, traumatic brain injury (TBI), vascular disease, vascular malformation, vascular type dementia movement disorder, Wilson's disease, or withdrawal syndrome.

The methods of treating a subject include providing a composition of the invention, as described above, to the subject. Providing may include administering the composition to the subject. The composition may be administered by any suitable means, such as orally, intravenously, enterally, parenterally, dermally, buccally, topically (including transdermally), by injection, nasally, pulmonarily, and with or on an implantable medical device (e.g., stent or drug-eluting stent or balloon equivalents). Preferably, the composition is provided orally. The composition may be provided under any suitable dosing regimen. For example, the composition may be provided as a single dose or in multiple doses. Multiple doses may be provided in provided separated by intervals, such as 4 hours, 6 hours, 8 hours, 12 hours, 24 hours, 2 days, 3 days, 4 days, 5 days, 1 week, 2 weeks, 3 weeks, 4 weeks, or more. Multiple doses may be provided within a period of time. For example, multiple doses may be provided over a period of 1 day, 2 days, 3 days, 4 days, 5 days, 1 week, 2 weeks, 3 weeks, 4 weeks, or more. The compositions may be provided repeatedly for a specified duration. For example and without limitation, the compositions may be provided for 1 week, 2 weeks, 3 weeks, 4 weeks, 6 weeks, 8 weeks, 12 weeks, 3 months, 4 months, 5 months, 6 months, 8 months, 10 months, 12 months or more.

EXAMPLES

Example 1

The ability of CV-10155 and SPNC-019 to modulate the activity of $GABA_A$ receptors of different $GABA_A$ was analyzed. CV-10155 and SPNC-019 have the following structures:

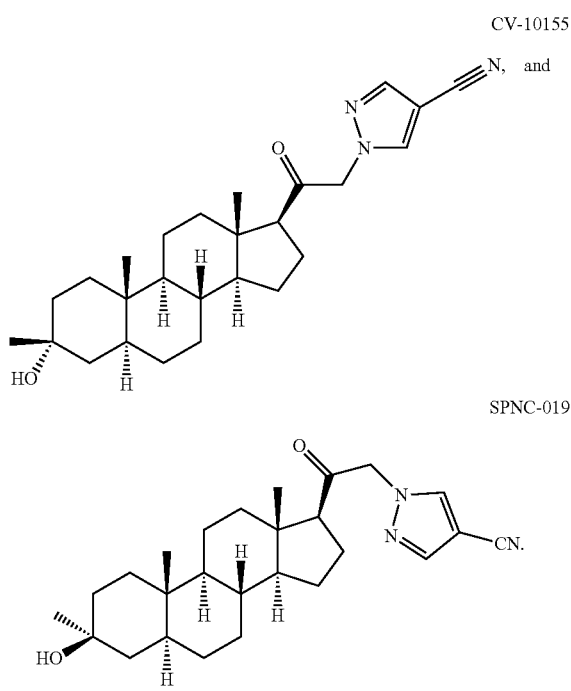

CV-10155

SPNC-019

Cells expressing the indicated GABA$_A$ receptor subtype were exposed to gamma-aminobutyric acid in the presence of varying concentrations of either CV-10155 or SPNC-019, calcium flux was measured using a fluorometric imaging plate reader (FLIPR), and EC50 values for compounds were determined. Results are provided in Table 1.

TABLE 1

| GABA$_A$ Compound | EC$_{50}$ (M) | |
|---|---|---|
| | CV-10155 | SPNC-019 |
| α1β1γ2 | 5.21E−07 | — |
| α1β2γ2 | 8.39E−07 | — |
| α1β3γ2 | 5.20E−07 | — |
| α2β1γ2 | 2.53E−07 | — |
| α2β2γ2 | 2.13E−07 | — |
| α2β3γ2 | 2.96E−07 | — |
| α3β1γ2 | 9.46E−07 | — |
| α3β2γ2 | 1.82E−06 | — |
| α3β3γ2 | 2.73E−07 | — |
| α4β1γ2 | 2.04E−07 | — |
| α4β3δ | 1.06E−07 | — |
| α4β3γ2 | 1.33E−06 | — |
| α5β1γ2 | 7.62E−07 | — |
| α5β2γ2 | 3.59E−07 | 1.198e−006 |
| α5β3γ2 | 1.30E−06 | 1.805e−006 |
| α6β1γ2 | 3.59E−07 | — |
| α6β2γ2 | 1.10E−06 | — |
| α6β3γ2 | 2.45E−07 | 1.766e−006 |

— value not measurable

CV-10155 showed some level of positive allosteric modulating activity in all of the GABA$_A$ receptor subtypes tested. In contrast, SPNC-019 had no modulating activity in 15 of the 18 GABA$_A$ receptor subtypes tested. The only structural difference between CV-10155 and SPNC-019 is the stereochemical configuration of the hydroxyl and methyl groups attached to the carbon atom at position 3 of the steroid core. Thus, the results show that a change in the stereochemistry of a single chiral center of a steroid-based compound dramatically alters ability of the molecule to modulate GABA$_A$ receptor activity. The results further indicate that the isomeric purity of neurosteroid compositions greatly impacts the utility of such compositions as therapeutic agents.

Example 2

The ability of various neurosteroids to compete with t-butylbicyclophosphorothionate (TBPS), a ligand for the picrotoxin binding site of GABA$_A$ receptors, was analyzed in International Publication No. WO 2016/061527. WO 2016/061527, pages 215-227. Compounds were assayed for binding to GABA receptors in membranes isolated from the cortices of rat brains. WO 2016/061527, page 216.

Among the neurosteroids analyzed was Compound 10, which has the following structure:

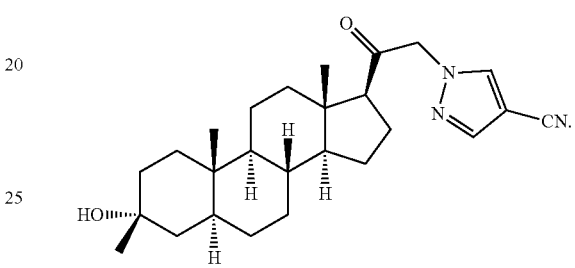

WO 2016/061527, page 106. Compound 10 is identical to the structure of Formula (II) and is a stereoisomer of the structure of Formula (I). Compound 10/Formula (II) and Formula (I) are stereoisomers that differ only in the configuration of the hydrogen atom bonded to the carbon atom at position 5: Compound 10/Formula (II) has a 5β configuration, whereas Formula (I) has a 5α configuration.

Another neurosteroid analyzed in WO 2016/061527 was Compound 121, which has the following structure:

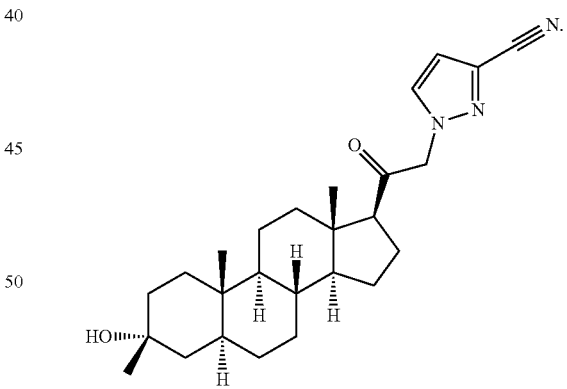

WO 2016/061527, page 150. Compound 121 is a regioisomer of the structure of Formula (I). Compound 121 and Formula (I) differ only in the positioning of the cyano substituent on the pyrazole ring: Compound 121 is substituted at the 3 position of the pyrazole ring, whereas Formula (I) is substituted at the 4 position of the pyrazole ring.

Compound 10 and Compound 121 are isomers that have two structural differences: the stereochemical configuration at carbon 5, and the position of the cyano substituent on the pyrazole ring.

Results of the analysis are provided in Table 1 of WO 2016/061527. WO 2016/061527, pages 217-227. Compound 10 has an $IC_{50}$ of <10 nM in the TBPS displacement assay, whereas Compound 121 has an $IC_{50}$ of 10-50 nM. WO 2016/061527, pages 217 and 221.

These results show that subtle structural differences in a neurosteroid can drastically affect binding of the molecule to $GABA_A$ receptors.

Example 3

The pharmacological efficacy of various neurosteroids for $\alpha 1\beta 2\gamma 2$ $GABA_A$ receptors and $\alpha 4\beta 3\delta$ $GABA_A$ receptors and was analyzed in International Publication No. WO 2016/061527. WO 2016/061527, pages 227-231. Compounds were tested for the ability to modulate GABA-mediated currents at a submaximal dose of agonist in LTK cells stably transfected with $\alpha 1\beta 2\gamma 2$ subunits and in CHO cells transiently transfected with $\alpha 4\beta 3\delta$ subunits WO 2016/061527, pages 227-228. Cells were incubated with GABA at 2 µM, which is the $EC_{20}$ for GABA, and 0.01 µM, 0.1 µM, 1 µM, or 10 µM neurosteroid. WO 2016/061527, pages 227-228.

Results of the analysis are provided in Table 2 of WO 2016/061527. WO 2016/061527, pages 229-231. Results are presented as the relative potentiation of GABA-mediated conductance in the presence of 10 µM neurosteroid compared to GABA-mediated conductance in the absence of neurosteroid. WO 2016/061527, page 228. Compound 121 at 10 µM displayed an efficacy of >500% for both $\alpha 1\beta 2\gamma 2$ $GABA_A$ receptors and $\alpha 4\beta 3\delta$ $GABA_A$ receptors. WO 2016/061527, page 229.

The results show that a regioisomer of Formula (I) displays no preferential modulation of $\alpha 4\beta 3\delta$ $GABA_A$ receptors over $\alpha 1\beta 2\gamma 2$ $GABA_A$ receptors. In particular, a compound that differs from Formula (I) only by the positioning of the cyano substituent on the pyrazole ring has comparable efficacy on the two $GABA_A$ receptor subtypes. Thus, the data give no indication that compositions containing a compound of Formula (I) can preferentially modulate $\alpha 4\beta 3\delta$ $GABA_A$ receptors over $\alpha 1\beta 2\gamma 2$ $GABA_A$ receptors or that such compositions can be administered at concentrations that modulate $\alpha 4\beta 3\delta$ $GABA_A$ receptors but not $\alpha 1\beta 2\gamma 2$ $GABA_A$ receptors. Consequently, nothing from the results suggests that compositions containing the compound of Formula (I) would be useful for treatment of conditions in which potentiation of $\alpha 4\beta 3\delta$ $GABA_A$ receptors but not $\alpha 1\beta 2\gamma 2$ $GABA_A$ receptors is beneficial.

In contrast, the data provided in Example 1 show that the compound of Formula (I) is substantially more active on $\alpha 4\beta 3\delta$ $GABA_A$ receptors than on $\alpha 1\beta 2\gamma 2$ $GABA_A$ receptors. Taken together, the results in the Examples demonstrate that subtle structural differences in a neurosteroid affect the ability of the molecule to potentiate specific subtypes of $GABA_A$ receptors. Therefore, it follows from the results that the isomeric purity of neurosteroid compositions can influence receptor subtype specificity and thus the utility of such compositions as therapeutic agents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method for treating a $GABA_A$ disorder, the method comprising providing to a subject having a $GABA_A$ disorder a pharmaceutical composition comprising an isomerically pure form of a compound of Formula (I):

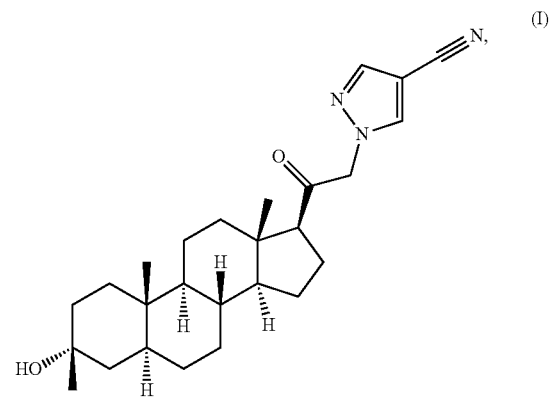

wherein:
the compound of Formula (I) is present in a therapeutically effective amount to preferentially potentiate an $\alpha 4\beta 3\delta$ $GABA_A$ receptor as compared to an $\alpha 1\beta 2\gamma 2$ $GABA_A$ receptor, and
the $GABA_A$ disorder is insomnia or a sleep disorder.

2. The method of claim 1, wherein the compound of Formula (I) preferentially positively modulates an $\alpha 4\beta 3\delta$ $GABA_A$ receptor as compared to an $\alpha 1\beta 2\gamma 2$ $GABA_A$ receptor.

3. The method of claim 2, wherein an $EC_{50}$ of the compound of Formula (I) for an $\alpha 4\beta 3\delta$ $GABA_A$ receptor is less than 50% of an $EC_{50}$ of the compound of Formula (I) for an $\alpha 1\beta 2\gamma 2$ $GABA_A$ receptor.

4. The method of claim 3, wherein an $EC_{50}$ of the compound of Formula (I) for an $\alpha 4\beta 3\delta$ $GABA_A$ receptor is less than 20% of an $EC_{50}$ of the compound of Formula (I) for an $\alpha 1\beta 2\gamma 2$ $GABA_A$ receptor.

5. The method of claim 1, wherein an $EC_{50}$ of the compound of Formula (I) for an $\alpha 4\beta 3\delta$ $GABA_A$ receptor is less than 500 nM.

6. The method of claim 1, wherein the composition is provided orally.

7. The method of claim 1, wherein the composition is provided in a single dose per day.

8. The method of claim 1, wherein the composition is provided in multiple doses per day.

9. The method of claim 1, wherein the composition is provided in a solid format.

10. The method of claim 9, wherein the solid format is selected from the group consisting of a capsule, powder, tablet, and troche.

* * * * *